(12) United States Patent
Chaigneau et al.

(10) Patent No.: US 9,366,694 B2
(45) Date of Patent: Jun. 14, 2016

(54) MICROSCOPE HAVING A MULTIMODE LOCAL PROBE, TIP-ENHANCED RAMAN MICROSCOPE, AND METHOD FOR CONTROLLING THE DISTANCE BETWEEN THE LOCAL PROBE AND THE SAMPLE

(71) Applicants: Ecole Polytechnique, Palaiseau (FR); Centre National de la Recherche Scientifique, Paris (FR)

(72) Inventors: Marc Chaigneau, Paris (FR); Akli Karar, Clamart (FR); Bernard Drevillon, Clamart (FR); Razvigor Ossikovski, Villebon-sur-Yvette (FR)

(73) Assignees: Ecole Polytechnique, Palaiseu (FR); Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 14/761,726

(22) PCT Filed: Jan. 13, 2014

(86) PCT No.: PCT/FR2014/050058
§ 371 (c)(1),
(2) Date: Sep. 23, 2015

(87) PCT Pub. No.: WO2014/114860
PCT Pub. Date: Jul. 31, 2014

(65) Prior Publication Data
US 2016/0003866 A1    Jan. 7, 2016

(30) Foreign Application Priority Data

Jan. 24, 2013 (FR) .................................... 13 50637

(51) Int. Cl.
*G01J 3/44* (2006.01)
*G01Q 10/00* (2010.01)
(Continued)

(52) U.S. Cl.
CPC . *G01Q 10/00* (2013.01); *G01J 3/06* (2013.01); *G01J 3/44* (2013.01); *G01N 21/658* (2013.01);
(Continued)

(58) Field of Classification Search
CPC ........... G01Q 10/00; G01Q 40/00; G01J 3/06; G01J 3/44
USPC .................................................. 356/300–445
See application file for complete search history.

(56) References Cited

U.S. PATENT DOCUMENTS 5,948,972 A * 9/1999 Samsavar ............... B82Y 35/00
73/105

OTHER PUBLICATIONS

International Search Report and Written Opinion for Application No. PCT/FR2014/050058 dated Mar. 5, 2014.
Kolodziejski, N. J. et al., *Versatile, High-Efficiency Tip-Enhanced Raman Spectroscopy (TERS) Instrumentation for End-User Applications*; Proc. of SPIE, vol. 7908, No. 1 (Feb. 10, 2011) pp. 1-8.
(Continued)

*Primary Examiner* — Abdullahi Nur
(74) *Attorney, Agent, or Firm* — Alston & Bird LLP (57) ABSTRACT

A multimode local probe microscope having a resonator, a first electrode, and a second electrode, an excitation source adapted to generate mechanical resonance in the resonator, a metal tip fastened to the resonator, movement mechanism for imparting relative movement between the local probe and a sample and adapted to bring the end of the tip to within a distance Z lying in the range 0 to 100 nm, and detector for detecting at least one electrical signal representative of friction forces at the terminals of said electrodes. The metal tip is electrically connected to the output second electrode and the microscopy apparatus includes amplifier and filter for amplifying and filtering signals relating to the friction forces and to the tunnelling current in a single electronic circuit, and configured for regulating the distance Z between the end of the tip and the surface of the sample.

10 Claims, 5 Drawing Sheets

(51) Int. Cl.
  *G01Q 10/04* (2010.01)
  *G01Q 20/04* (2010.01)
  *G01Q 30/02* (2010.01)
  *G01Q 60/04* (2010.01)
  *G01Q 60/16* (2010.01)
  *G01Q 60/26* (2010.01)
  *G01N 21/65* (2006.01)
  *G01J 3/06* (2006.01)
  *G01Q 40/00* (2010.01)

(52) U.S. Cl.
  CPC .............. *G01Q 10/045* (2013.01); *G01Q 20/04* (2013.01); *G01Q 30/02* (2013.01); *G01Q 40/00* (2013.01); *G01Q 60/04* (2013.01); *G01Q 60/16* (2013.01); *G01Q 60/26* (2013.01)

(56) References Cited

OTHER PUBLICATIONS

Ndobo-Epoy, J.-P. et al., *Shear Force Microscopy With a Nanoscale Resolution*, Ultramicroscopy 103 (Jun. 1, 2005) 229-236.

Woszczyna, M. et al., *Investigations of Local Electrical Properties Using Tunneling/Atomic Force Microscope With a Quartz Tuning Fork Nearfield Sensor*, Vacuum, vol. 82, No. 10 (Jun. 3, 2008) pp. 982-987.

Woszczyna, M. et al., *Tunneling/Shear Force Microscopy Using Piezoelectric Tuning Forks for Characterization of Topography and Local Electric Surface Properties*, Ultramicroscopy, vol. 110, No. 7 (Jun. 1, 2010) 877-880.

Seo, Y. et al., *Electrostatic Force Microscopy Using a Quartz Tuning Fork*, Appl. Phys. Lett. 80, 4324 (2002).

Karrai et al., Phys. Rev. B 62, 13174 (2000).

* cited by examiner

MICROSCOPE HAVING A MULTIMODE LOCAL PROBE, TIP-ENHANCED RAMAN MICROSCOPE, AND METHOD FOR CONTROLLING THE DISTANCE BETWEEN THE LOCAL PROBE AND THE SAMPLE

FIELD

In general manner, the present invention relates to the field of local probe microscopy.

BACKGROUND

Local probe microscopy, or scanning microscopy, is based on measuring a physical magnitude while scanning a tip at a very short distance from the surface of a sample. Local probe microscopy makes it possible to obtain an image of the surface topography of a sample with spatial resolution better than the resolution of an optical microscope.

There exist various techniques for local probe microscopy. Mention may be made in particular of the atomic force microscope (AFM), of the scanning tunnelling microscope (STM), and of the friction- or shear-force microscope (SFM).

The scanning tunnelling microscope has an electrically conductive tip that serves to collect electric current generated by the tunnel effect when the tip is brought to a very short distance (in the range 0 to 5 nanometers (nm)) from the surface of a conductive sample. An STM generally comprises tunnelling current regulator means based on imparting nano movements between the sample and the tip along the Z axis of the tip with the help of a piezoelectric ceramic, the Z axis generally extending transversely to the surface of the sample. The value of the position occupied along the Z axis for servo controlling the tunnelling current as a function of XY scanning of the tip is then representative of variation in the surface relief of the sample. The scanning tunnelling microscope makes it possible to provide an image of the surface topography with sub-nanometer resolution. An STM requires a conductive tip, generally a metallic tip, made of nickel or of tungsten. Nevertheless, an STM is limited to being applied to samples that are conductive.

An atomic force microscope (AFM) is based on using repulsion and attraction forces between atoms at the surface of the sample and atoms at the end of the tip, which is of nanometer size. An atomic force microscope generally comprises a lever having a tip made of silicon or of silicon nitride, possibly covered in a deposit of metal. In conventional manner, the movement of the tip is observed by measuring the deflection of a laser beam reflected on the lever of the tip. The distance between the end of the tip and the surface of the sample is controlled by very fine detection of attraction and repulsion conditions, so as to avoid any contact between the tip and the surface. An AFM can be used to observe a sample of any type.

A shear-force microscope (SFM) comprises a resonant or vibrating local probe, generally comprising a piezoelectric oscillator (or resonator, generally of tuning fork shape) made of quartz and having a fine tip fastened thereto. When excited at its resonant frequency $f_0$ (in the range 15 kilohertz (kHz) to 30 kHz) by applying an electric signal to its terminals or by mechanical excitation, the resonator induces small-amplitude ($\approx$1 nm) vibration of the tip transversely to the Z axis of the tip. When the vibrating point is brought up to the surface of a sample to within a distance of less than one hundredth of a nanometer, a modification is observed in the parameters of the resonance of the resonator under the action of friction forces and/or shear forces between the end of the vibrating tip and the surface of the sample. This modification of the resonator gives rise to damping of the amplitude of the resonator and to a shift in the resonant frequency or to a reduction in the quality factor (Q factor) of the resonator. The imaging mode consists in scanning the tip parallel to the surface of the sample and in measuring the amplitude of the current that results from the excitation, which is itself proportional to the amplitude of the mechanical oscillation of the branches of the resonator. Various types of tip are used for SFM: a tapering optical fiber or a metal tip. One of the limits of shear-force microscopy is that the distance between the tip and the surface of the sample is generally unknown, which distance usually lies in the range about 20 nm to about 100 nm. This distance is generally estimated by detecting the instant that contact is made between the tip and the sample, leading to destruction of the end of the tip, which spoils its spatial resolution. A shear-force microscope can be used to map the surface topography of any type of sample, but it provides a topographic image with spatial resolution in the XY plane that is relatively degraded because of the oscillations of the tip.

There also exist microscopes, known as multimode local probe microscopes, that combine various operating modes for local probe microscopy.

Thus, the publication by J-P. Ndobo-Epoy et al. "Shear-force microscopy with a nanoscale resolution", Ultramicroscopy 103 (2005), pp. 229-236 describes a shear-force microscope having a resonant local probe comprising a tuning fork with a nickel tip adhesively bonded thereto. A first electronic circuit is connected to the two electrodes of the tuning fork in order to measure the amplitude of oscillation. A second electronic circuit is connected to the tip in order to measure the tunnelling current between the nickel tip and a gold sample. According to the authors of that publication, having one of the branches of the resonator loaded by the tip and by the adhesive gives rise to a considerable reduction in the quality factor of the resonator ($Q \approx 100$). Furthermore, that device does not make it possible to avoid contact between the tip and the surface of the sample, nor does it make it possible to calibrate accurately the distance between the end of the tip and the surface of the sample for distances of less than 20 nm, because of almost complete damping of the oscillation amplitude of the branches of the tuning fork.

Furthermore, the publication by Yeong Seo et al. "Electrostatic force microscopy using a quartz tuning fork", Appl. Phys. Lett. 80, 4324 (2002) describes an electrostatic force microscope based on a resonant tuning fork and a nickel tip fastened to an electrode of the tuning fork. The tip is used either in contact mode with the surface of the sample in order to apply a constant electrostatic force locally, or alternatively at a constant distance of 50 nm in order to measure an electrostatic force between the end of the tip and the surface of the sample.

The document by M. Woszczyna et al., "Tunneling/shear force microscopy using piezoelectric tuning forks for characterization of topography and local electric surface properties", Ultramicroscopy 110, 877 (2010), describes a microscope with a local resonant probe comprising a tungsten tip fastened on a quartz resonator in the form of a two-branch tuning fork. The tuning fork is excited at its resonant frequency by mechanical excitation. Two electrodes on the branches of the tuning fork provide an electrical measurement of the amplitude of oscillation of its branches by using the piezoelectric effect that is naturally present in the quartz crystal. Those two electrodes are connected to a preamplifier to make it possible subsequently to amplify the signal relating to the shear forces between the tip and the surface of the sample. A third electrode electrically connects the tip to a current-to-voltage converter for measuring the tunnelling current between the tip and the surface of the sample, which is covered in a thin layer of gold or of diamond. That microscope makes it possible to measure independently the current due to the tunnel effect and the lateral shear force at a single point of the surface of the sample. Nevertheless, that configuration has the effect of drastically degrading the quality factor of the tuning fork (by a factor of 10), thereby reducing the sensitivity of the microscope in friction force conditions. The system is thus observed to become more rigid, which is harmful for regulating the distance between the tip and the sample, in particular for distances of less than about one-twentieth of a nanometer. In addition, that device does not make it possible to calibrate accurately the distance between the tip and the sample, which distance is merely estimated. It is true, that Karrai et al. (Phys. Rev. B 62, 13174, 2000) disclose topographic measurement revealing atomic-scale roughness of a graphite sample under a vacuum in constant tunnelling current mode, with a tuning fork that is excited at its resonant frequency. Nevertheless, that prior art system requires an evacuated environment, with its operation under atmospheric pressure being greatly degraded.

Furthermore, near field microscopy can advantageously be coupled with various analysis techniques. In particular, the tip enhanced Raman spectroscopy (TERS) or nano Raman technique relates to coupling a Raman spectroscopy apparatus with a local probe microscope having a tip made of noble metal or covered in a noble metal. Enhancement is observed of the Raman signal emitted locally at a point of the surface of a sample when the excitation laser beam of the Raman spectrometer is focused on the end of the tip of the near field microscope that has been brought to within a few nanometers of the surface of the sample, with this being due to local amplification of the electromagnetic field. The tip-to-sample distance is generally regulated by an AFM, but topographical resolution is then degraded, given the layer of metal deposited on the tip, or else by means of an STM, however the need to perform regulation on the tunnelling current makes it possible to use TERS analysis on conductive samples only. This means that the TERS technique is very difficult to implement.

It is desirable to develop a local probe microscope, in particular for TERS applications, in which the distance between the end of the tip and the surface of the sample lies in the range 0 to about 20 nm, with this distance being controlled and calibrated. A first difficulty is bringing the tip up to the surface of the sample to within a very short distance of only a few nanometers. Another difficulty is controlling this very short distance during scanning by the tip. Yet another difficulty is avoiding contact between the end of the tip and the surface of the sample, since any contact is likely to damage the nanometer-size end of the tip. There does not exist a TERS Raman spectroscope that operates with a local probe of the friction-force type and that enables the distance between the end of the tip and the surface of a sample to be controlled and calibrated accurately within a range of distances extending from 0 to about 20 nm, and preferably less than 10 nm, without involving contact between the end of the tip and the surface.

SUMMARY

One of the objects of the invention is to provide a multimode microscope with a local probe in which the distance between the end of the tip and the surface of the sample can be servocontroled, in particular for a distance that is short, i.e. less than a few tens of nanometers.

Another object of the invention is to propose a tip enhanced Raman spectroscopy apparatus with a distance between the end of the tip and the surface of the sample that is very short and regulated.

Yet another object of the invention is to provide a method of calibrating the distance between the end of a tip of a local probe microscope, in particular a friction-force microscope, and the surface of a sample, when said distance lies in the range 0 to 10 nm.

An object of the present invention is to remedy the drawbacks of prior art local probe microscopes and to propose more particularly a multimode local probe microscope having a resonator (preferably a quartz tuning fork) having an input first electrode and an output second electrode arranged on the resonator, excitation means adapted to generate mechanical resonance in the resonator (the tuning fork), a metal or metal-plated tip having an end of nanometer dimensions, the tip being fastened to the resonator, and movement means for imparting relative movement between the resonator and the sample, the movement means being adapted to bring the end of the tip up to a distance Z lying in the range 0 to 100 nm from the surface of the sample.

According to the invention, said metal tip is electrically connected to said output second electrode, said output second electrode forming a common electrical contact point for collecting firstly a first electrical signal representative of friction forces between the end of the tip and the surface of the sample, and secondly a second electrical signal relating to a tunnelling current between the end of the tip and the surface of the sample; and the microscope includes amplifier means electrically connected to said output second electrode, said amplifier means being adapted to amplify simultaneously the first signal relating to friction forces and the second signal relating to the tunnelling current, processor means adapted to process separately firstly the first signal relating to friction forces and secondly the second signal relating to the tunnelling current, and regulator means adapted to regulate the distance Z between the end of the tip and the surface of the sample, regulation in a first mode being as a function of the first signal representative of friction forces, and in a second mode being as a function of the second signal relating to the tunnelling current.

The device makes it possible to regulate the distance Z between 0 and a few tens of nanometers, while avoiding any mechanical contact between the end of the tip and the surface of the sample.

The local probe microscope of the invention makes it possible to measure simultaneously the friction forces and the tunnelling current, and it can operate in multimode manner: in a first mode, the friction forces are measured while regulating the distance between the tip and the sample on the basis of the tunnelling current; in another mode, the tunnelling current is measured while regulating the distance between the tip and the sample on the measurement of the friction forces. The configuration of the local probe avoids connecting the metal or metal-plated tip to an external conductor wire in order to collect a signal representative of friction forces, thereby making the local probe less sensitive to external disturbances and making it possible to keep the quality factor of the resonator at a high value. Using a common summing point for collecting and amplifying a tunnelling current signal and a signal representative of friction forces thus makes it possible to improve the signal-to-noise ratio for both of the signals.

According to particular and advantageous aspects, the multimode local probe microscope comprises:

common amplifier means for amplifying both signals, comprising a low noise preamplifier for simultaneously amplifying the current that results from exciting the resonator and the tunnelling current;

the processor means comprise active or passive electronic filter means connected to the second electrode, said filter means being adapted to separate firstly the first signal relating to friction forces and secondly the second signal relating to the tunnelling current as a function of their respective frequencies, for subsequent regulation processing;

filter means comprise a bandpass filter adapted to filter said first signal relating to friction forces spectrally (e.g. around $f_0=25$ kHz), preferably before the input to a synchronous detector system ("lock in"); and a lowpass filter adapted to filter said second signal relating to the tunnelling current spectrally (preferably the range 0 to 10 kHz);

the tip is made of or covered in a metal preferably selected from gold and silver;

the microscope includes means for (XY) scanning the tip relative to the surface of the sample; and the quartz resonator in the form of a tuning fork (or resonant fork) having a first branch and a second branch, the input first electrode being arranged on the first branch, and the output second electrode being arranged on the second branch.

Advantageously, the filter means comprise a lowpass filter having a cut-off frequency at 10 kHz relating to the tunnelling current, and a bandpass filter for passing a signal around $f_0$ relating to the friction and/or shear forces.

The invention also provides a tip enhanced Raman microscope comprising a multimode local probe microscope according to an above described embodiment, said Raman microscope comprising a Raman spectrometer, means for focusing an excitation laser beam on the end of the tip of the microscope, and detector means for detecting a Raman diffusion signal generated by the sample in the vicinity of said tip.

In a preferred embodiment, the tip enhanced Raman microscope comprises means for triggering detection of the Raman diffusion signal and synchronisation means that are connected firstly to the means for triggering detection and secondly to the means for regulating the distance Z between the tip and the sample in such a manner as to synchronise said means for triggering detection of the Raman diffusion signal and said regulator means while bringing the tip to a predetermined distance $Z_0$-$\Delta Z$.

The invention also provides a method of calibrating the distance Z between of the surface of a sample and the end of the tip of a multimode local probe microscope according to an above described embodiment, said calibration method comprising the following steps:

generating mechanical resonance in the resonator suitable for producing vibration at the end of the local probe tip;

bringing the tip towards the surface of a reference sample;

simultaneously detecting a first electrical signal relating to friction forces between the end of the tip and the surface of the reference sample, and a second signal relating to a tunnelling current generated between the end of the tip and the surface of the reference sample;

for said reference sample, determining a reference distance at which a reference tunnelling current appears, said reference distance corresponding to a distance for which said second signal is greater than or equal to a predetermined tunnelling current threshold for said reference sample;

measuring a reference value of the first signal relating to friction forces on said reference sample at said reference distance at which tunnelling current appears; and regulating on the first signal relating to friction forces for any type of sample of the same nature as the reference sample as a function of said reference value for the first signal relating to friction forces on said reference sample at said reference distance at which tunnelling current appears.

Advantageously, said reference distance is greater than zero and less than or equal to 10 nm, and preferably less than 5 nm. This calibration is performed on a conductive sample, and is then transferable to any other type of sample, which may be semiconductive or insulating (e.g. glass).

Advantageously, the local probe microscope includes means for measuring the variation in at least one parameter of the resonator during XY scanning of said tip, and processor means adapted to extract from said variation an image that is representative of the surface topography of the sample, with XY spatial resolution. Preferably, said measurement means also include means for measuring a tunnelling current between the end of the tip and a point of the surface of a sample, when said tip end is placed at a nonzero distance in order to avoid any damage to said tip.

Advantageously, the amplifier means comprise a low noise amplifier.

The invention finds a particularly advantageous application in tip enhanced Raman spectroscopy, in which a local probe microscope is coupled to a Raman spectrometer for performing Raman spectrometer measurements with nanometric spatial resolution.

The present invention also relates to the characteristics that appear from the following description and that may be considered in isolation or in any technically feasible combination.

BRIEF DESCRIPTION OF THE DRAWINGS

This description given by way of nonlimiting example makes it possible to understand better how the invention can be implemented, with reference to the accompanying drawings, in which.

DETAILED DESCRIPTION

Device

Figures 1, 2, 4:
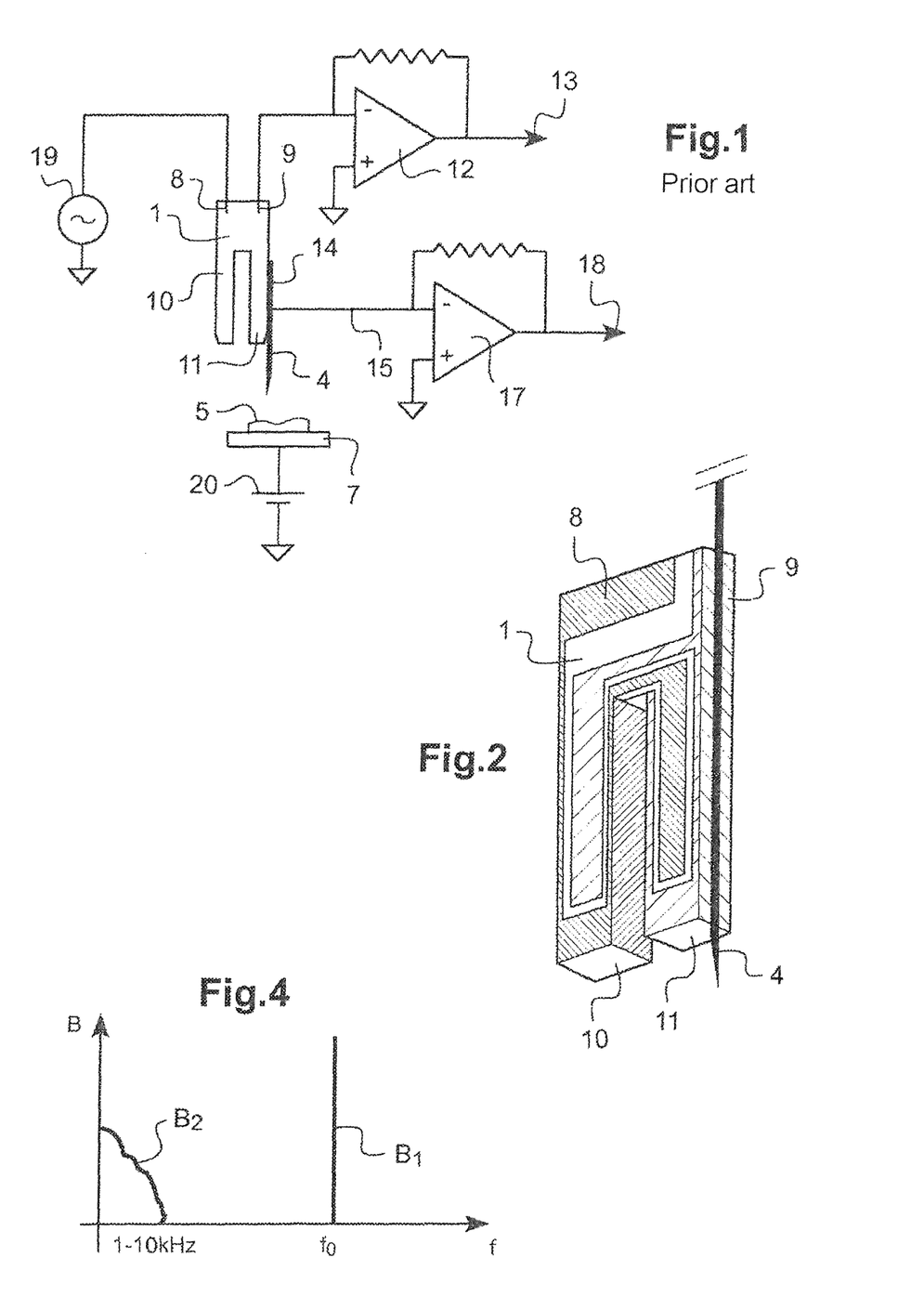
FIG. 1 shows the electronic circuit diagram of a prior art tuning fork probe for a shear-force microscope and for tunnelling current detection.
FIG. 2 is a diagram showing a perspective view of a tuning fork probe for a shear-force microscope in an embodiment of the invention.
FIG. 4 is a diagram showing the frequency distribution of signals representative respectively of a tunnelling current and of a quartz resonator

FIG. 1 is a diagram showing a probe of a local probe microscope of the shear-force type of the prior art together with its electronic amplifier circuits, in a configuration in which it is desired to pick up a current (field emission current or tunnelling current) between the end of the tip and the surface of the sample. In this example, the probe shown has a resonator 1 in the form of a tuning fork with a first branch 10 and a second branch 11. Preferably, the resonator 1 is a quartz crystal resonator analogous to a quartz resonator used in watchmaking. The probe has a metal tip 4, e.g. made of gold, that is fastened to one of the branches 11 of the tuning fork so that a tapering end of the tip projects beyond the end of the branch 11, approximately by a few tenths of a millimeter in the direction Z. A function generator 19 serves to excite the resonator 1 electrically in the vicinity of its resonant frequency so that the branches of the tuning fork vibrate in the XY plane. The resonant frequency $f_0$ of the probe is generally a few tens of kilohertz, typically $f_0$=32 kHz when the resonator does not have a tip (is not loaded), and by way of example $f_0$=25 kHz when the resonator is loaded with a tip. A sample 5 rests on a conductive sample-carrier 7. A voltage source 20 serves to apply a direct current (DC) voltage to the sample 5. The probe has a first electrode 8 placed on the first branch 10, and a second electrode 9 placed on the second branch 11. The first electrode 8 and the second electrode 9 are electrically connected to an electronic circuit 12. Advantageously, the electronic circuit 12 serves to amplify and convert into a voltage the current that results from exciting the resonator at its resonant frequency. The signal 13 output by the converter 12 can then be processed by an electronic system in order to extract amplitude and phase signals therefrom that are representative of the friction and/or shear forces between the probe 1 and the surface of the sample 5 when the probe is close to the surface of the sample 5.

Furthermore, in the prior art device shown in FIG. 1, the tip 4 stuck to the branch 11 without electrically contacting the electrode 9 is connected to another electrical contact 14. An electric wire 15 connects the electrical contact 14 of the tip 4 to another electronic amplifier circuit 17 serving to amplify a tunnelling current as picked up between the tip 4 and the sample 5, and to deliver a signal 18 at the output from the electronic circuit 17.

The prior art device shown in FIG. 1 makes it possible, ideally under vacuum pressure conditions, to measure the tunnelling current between the end of the tip 4 of the vibrating probe 1 and a biased sample 5. Nevertheless, the device and the method of calibrating the probe shown in FIG. 1 generally rely on detecting contact between the end of the probe and the surface of the sample in order to calibrate the position Z=0, and that can damage the end of the tip and degrade its imaging capacity.

An observation forming part of the present invention is that the quality factor of a vibrating probe as shown in FIG. 1 is highly degraded by the metal tip having added thereto an electrical contact 14 and an additional wire 15 for detecting the tunnelling current, with degradation being the result both of the probe being stiffened and also of greater mechanical asymmetry of the resonator. A local probe microscope as shown in FIG. 1 presents results that are degraded in friction force mode and is sensitive to surrounding interfering electromagnetic radiation.

A second observation forming part of the present invention is that the device shown in FIG. 1 has two distinct electronic preamplifier circuits 12 and 17.

A third observation is that the prior art probe constituted by the resonator 1 and the tip 4 has three distinct electrical contacts: the first electrode 8, the second electrode 9, and the electrical contact point 14 on the tip 4.

FIG. 2 is a diagram showing a perspective view of a probe comprising a resonator 1 in the form of a tuning fork in an embodiment of the invention. The probe comprises a tuning fork, preferably made of quartz, a first electrode 8 being placed on the first branch 10, and a second electrode 9, or output electrode, being placed on the second branch 11. A tapering metal (or metal-plated) tip 4 is fastened to the second branch 11 of the tuning fork. By way of example, the tip 4 is stuck to the second branch 11 in such a manner that its tapering end projects beyond the end of the second branch by a few tens to a few hundreds of micrometers. Advantageously, the tip 4 is made of or is covered in a noble metal, and is preferably made from a wire of gold or of silver. The tip 4 is in electrical contact with the second electrode 9 of the tuning fork. The tip 4 is not connected by a conductor wire to another electronic circuit, thereby avoiding weighing down the probe in asymmetric manner and avoiding stiffening it, thus making it possible to conserve an excellent quality factor for the tuning fork. Furthermore, the local probe shown in FIG. 2 is particularly compact.

Figure 3A:
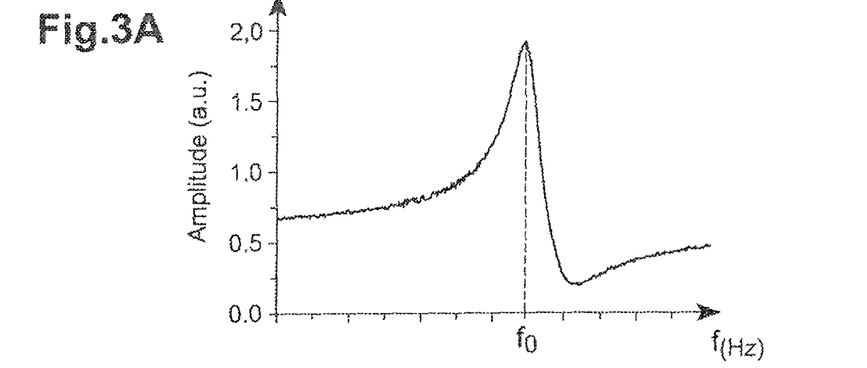
FIG. 3A shows the resonance amplitude of the resonator in an embodiment of the invention prior to compensation.
Figure 3B:
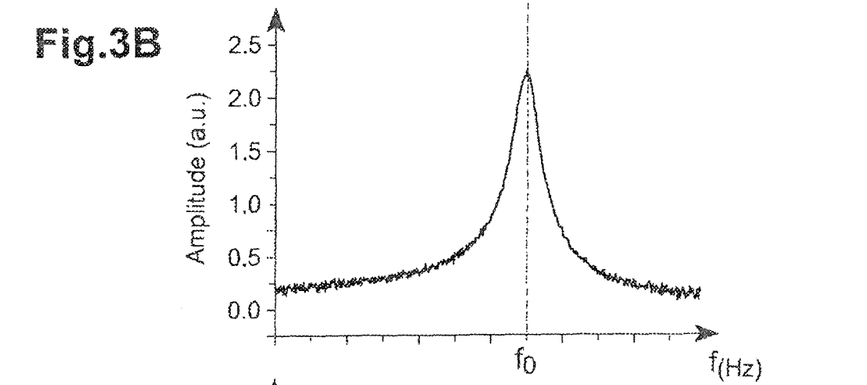
FIG. 3B shows the resonance amplitude of the resonator, after compensation.
Figure 3C:
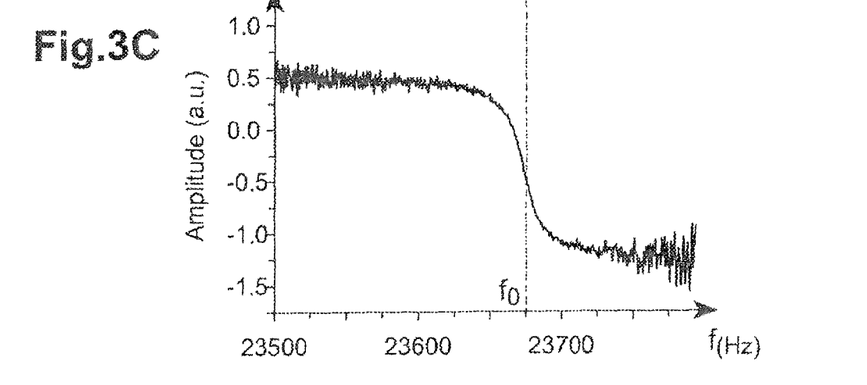
FIG. 3C shows the corresponding phase of the resonator.

A generator connected to the electrodes 8 and 9 makes it possible to excite the vibrating probe in the vicinity of its resonant frequency $f_0$ (about 25 kHz when the probe is provided with the tip). FIG. 3A shows the amplitude of the resonance spectrum as a function of frequency f (Hz) for a resonator mounted with a tip stuck on the output electrode 9. At frequencies higher than the resonant frequency, it can be seen that anti-resonance appears as a result of stray capacitance. In order to eliminate the anti-resonance created by the stray capacitance and the resulting deformation of the resonance (see FIG. 3A), electronic compensation means, e.g. a parallel-connected variable capacitance, are added to the summing point of the electronic circuit for processing the signals (see FIG. 5A). FIGS. 3B-3C show the resonance spectrum after the resonator has been compensated in this way (FIG. 3B shows the spectrum in terms of amplitude and FIG. 3C shows the spectrum in terms of phase, respectively). It can be seen that the quality factor Q (the ratio of the resonant frequency $f_0$ divided by the half height width of the resonance) is not degraded, unlike a prior art probe such as that shown in FIG. 1.

Thus, the second electrode 9 of the probe as shown in FIG. 2 collects simultaneously both the tunnelling current and also a current that results from the oscillation of the resonator, unlike a probe as shown in FIG. 1, in which these currents are collected respectively from separate contact points.

Another observation forming part of the invention is that the frequency distribution of signals representative respectively of tunnelling current and of a quartz resonator enables these signals to be separated by frequency (cf FIG. 4). The signal $B_1$ representative of the oscillations of the vibrating probe remains in the frequency band around the resonant frequency specific to the resonator, around $f_0$=25 kHz, while a signal representative of the tunnel effect current is situated in the low frequency range, being limited to about 2 kHz. A single electronic circuit connected to the terminals of the electrodes 8 and 9, and having a single common preamplifier connected to the output electrode 9 of the local probe, then makes it possible simultaneously a to collect and to amplify both a tunnelling current between the tip and an electrically biased sample, and also a current representative of the oscillation of the vibrating probe, in amplitude and/or in phase. This configuration makes multimode operation of the local probe microscope possible, i.e. makes it possible for it to operate in tunnelling current mode and/or in friction force mode.

Figure 5A:
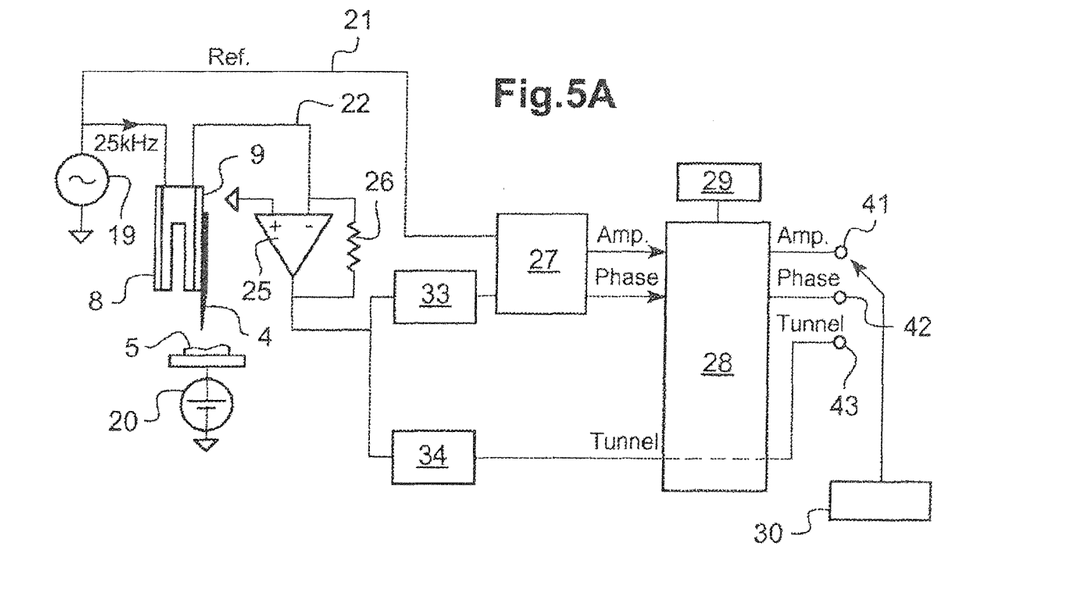
FIG. 5A shows an electronic circuit diagram of a device having a resonant local probe in a preferred embodiment of the invention.

FIG. 5A shows an electronic circuit diagram of a device having a resonant local probe in a preferred embodiment of the invention. A voltage source 19 is connected to the electrodes 8 and 9 in order to excite the probe 1 in the vicinity of its resonant frequency ($f_0 \approx 25$ kHz). A conductive line 21 serves to transmit the excitation reference frequency to a synchronous detector system 27 ("lock in"). A sample 5 rests on a conductive sample-carrier 7. A voltage source 20 serves to apply a preferably-constant DC bias voltage of a few millivolts to a few volts to the sample 5.

In FIG. 5A, a preamplifier 25 (a low-noise current-to-voltage converter together with a resistor 26) is connected directly by a conductive line 22 to the output electrode 9 that is electrically connected to the metal tip 4. A filter 34, e.g. a lowpass filter, and a filter 33, e.g. a bandpass filter, are arranged at the output from the preamplifier 25. At the output from the filter 34, a signal is obtained that is representative of the tunnel effect current as filtered from the 25 kHz signal. At the output from the bandpass filter 33, a signal is obtained that is representative of the friction and/or shear forces, which signal is injected into the synchronous detector system 27 ("lock in") in order to provide the amplitude and the phase of the vibrating probe around the resonant frequency of the oscillator. The electronic circuit 28 as a digital acquisition card, comprising an internal real-time processor together with high-resolution analog-to-digital and digital-to-analog converters (ADC and DAC) and digital-to-analog converters (DAC). The electronic circuit 28 is controlled by the computer 29 and it delivers respectively a first signal representative of the amplitude of the vibrating probe on a first output 41, a second signal representative of the phase of the vibrating probe on a second output 42, and a third signal representative of a tunnel effect current on a third output 43. All of the signals are transmitted to a computer in order to construct an image during a scan. Each of these three signals 41, 42, and 43 can be selected as a variable for regulating the position of the tip 4 above the sample.

A device based on the circuit diagram of FIG. 5A thus makes it possible to produce a multimode microscope capable of operating either in friction force mode, or in tunnelling mode, or indeed in a mode combining both friction force and tunnelling current, since these two tools do not interfere with each other.

The electronic circuit of FIG. 5A serves to amplify simultaneously the small signals of the tunnelling current (lying in the range a view pico amps to a few nano amps) and of the resonator, while using a single preamplifier 25. The summing point of the amplifier is situated ahead of the preamplifier 25, on the conductor line 22. This electronic circuit, which is robust against surrounding interference, makes it possible optionally to add to the summing point an electronic circuit for compensating the anti-resonance of the resonator, and possibly also for compensating for interference due to mains (e.g. 50 Hz).

In particularly advantageous manner, the electronic circuit can be integrated as close as possible to the local probe, directly in a multimode microscope having an "active" head, in order to limit interfering noise.

The use of an electrical contact between the tip 4 and the output electrode 9, which represents a common electrical contact point for detecting both the tunnelling current and also the resonance signal, makes the local probe microscope insensitive to dispersion in the contact resistance between the tip 4 and the electrode 8 (by way of example, a bias voltage for the sample of about 1 volt (V) for a tunnelling current of about 1 nanoamp (nA) induces a tunnelling resistance of about 1 gigohm (G$\Omega$), which remains much greater than a contact resistance of about 1 kilohm (k$\Omega$), even if this resistance is not reproducible from one tip to another).

A piezoelectric movement system 30, e.g. a piezoelectric actuator connected to the probe 1, serves to modify the distance Z by imparting nano movements between the end of the tip 4 and the surface of the sample 5. The regulation electronics controlling these nano movements 30 may be connected to one of the three outputs 41, 42, and 43 in order to perform regulation on one of the amplitude or phase signals coming from the vibrating probe, or on the tunnelling current, and to perform measurement on the other one of the signals as a function of the scanning of the probe over the surface of the sample.

The device of FIG. 5A relies on using a single common electronic circuit connected to only two electrical contact points 8 and 9 on the probe 1. A local probe multimode microscope is thus provided that operates on simultaneously detecting both friction and/or shear forces and also the tunnelling current, and on regulating distance on the basis of one or the other of these signals. The multimode local probe microscope with the invention can operate at atmospheric temperature and pressure.

Figure 5B:
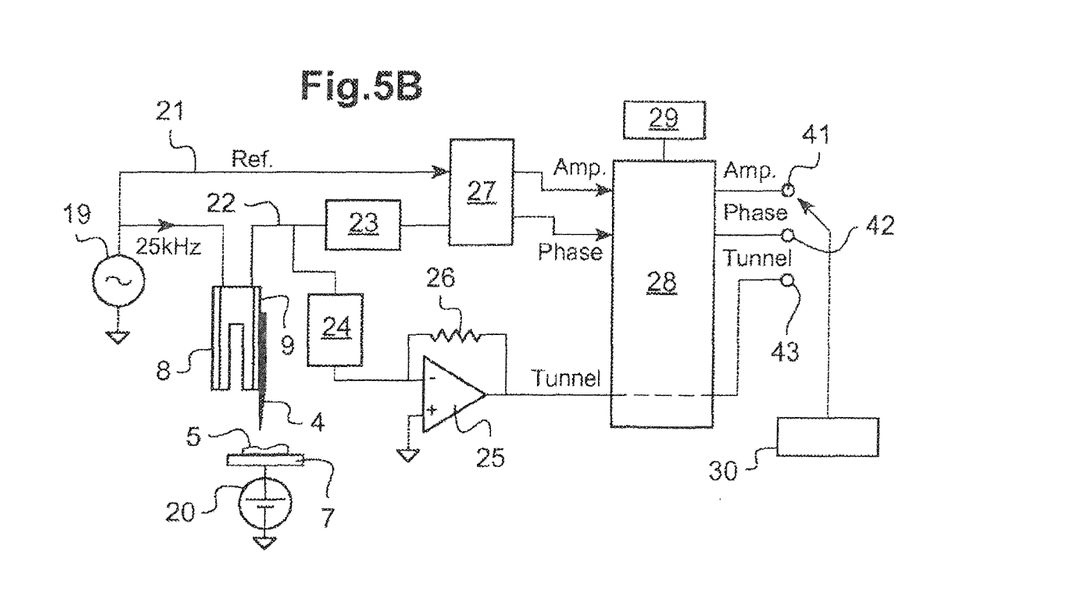
FIG. 5B shows an electronic circuit diagram of a device having a resonant local probe in an alternative to the embodiment of FIG. 5A.

FIG. 5B shows an electronic circuit for a resonant local probe device in a variant embodiment of the invention, with the same reference signs representing the same elements as in FIG. 5A. A conductive line 22 connects the output electrode 9 to a first filter 23 and to a second filter 24. Advantageously, the first filter 23 is a bandpass filter centered about the frequency of the oscillator, e.g. 25 kHz. At the output from the first filter 23, a signal is obtained that is representative of friction forces, which signal is then injected into a synchronous detector 27 ("lock in"). Advantageously, the second filter 24 is a lowpass filter having an output providing a signal that is representative of the tunnel effect current as filtered from the 25 kHz signal. The filters 23 and 24 serve to decouple respective pass bands for signals relating firstly to the vibrating probe and secondly to the tunnelling current. At the output from the second filter 24, a preamplifier 25 (a low noise current-to-voltage converter and resistor 26) serves to amplify a signal representative of the tunnel effect current between the tip 4 and the biased sample 5, when the sample 5 is conductive or semi-conductive. A real-time electronic circuit 28, comprising a digital acquisition card (internal real-time processor together with high resolution analog to digital and digital to analog converters (ADC and DAC) under the control of a computer 29, delivers respectively a first signal representative of the amplitude of the vibrating probe on a first output 41, a second signal representative of the phase of the vibrating probe on a second output 42, and a third signal representative of a tunnel effect current on a third output 43.

Calibration Method

It is also proposed to calibrate the distance Z between the end of the tip 4 and the surface of the sample 5 in a friction force (shear-force) mode of regulation without damaging physical contact between the tip and the surface of the sample. The calibration method relies on detecting the tunnelling current flowing between the surface of the sample 5 and the end of the vibrating tip fastened to the output electrode 9 of the tuning fork probe 1, while simultaneously detecting transverse oscillation of the tip.

Figure 6:
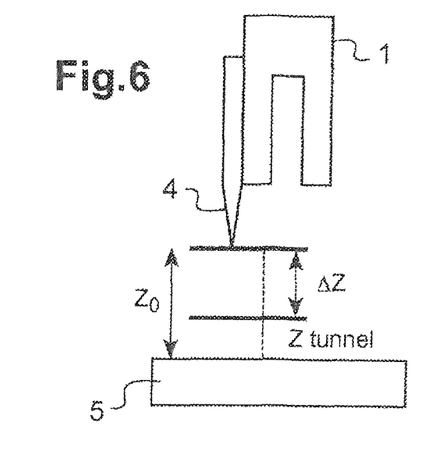
FIG. 6 is a diagram showing a local probe of a multiple microscope of the invention, operating by detecting friction forces and tunnelling current at different distances from the surface of the sample.

FIG. 6 is a diagram showing a local probe of a multimode microscope of the invention, as described with reference to FIG. 2. The distance Z between the end of the tip 4 and the surface of the sample 5 is to be regulated in real time. The main difficulty lies in the fact that the regulation distance $Z_0$ is not accurately known in friction force (shear-force) mode. However, in certain applications, in particular in tip-enhanced Raman spectroscopy, it is desired to reduce the distance Z to a distance that is less than or equal to about 5 nm in order to regulate this distance accurately, while avoiding any contact between the end of the tip 4 and the surface of the sample 5, even while the tip is vibrating in the XY plane.

As explained in detail above, the device described with reference to FIGS. 2 and 5A (or 5B) makes it possible to measure simultaneously the signals from the friction force microscope (shear-force mode) and the tunnelling current (STM mode) and to choose to regulate the position of the tip on the detected friction forces while simultaneously displaying the tunnelling current, or vice versa.

The calibration method comprises the following steps:

calibrating a distance $Z_{tunnel}$ by measuring the tunnelling current on a reference conductive sample (selected from reference samples of various kinds made of metal, of doped semiconductor, of conductive glass);

acquiring the amplitude of the signal relating to the friction forces while regulating the distance between the tip and the reference sample by means of the tunnelling current, i.e. with reference to $Z_{tunnel}$; and regulating (or servo controlling) the distance Z to a value $Z_{tunnel}$ while the microscope is operating in friction force (shear-force) mode, using the amplitude value as measured during the preceding step.

Thereafter, this regulation can be used for any other sample of the same nature as the selected reference sample.

Advantageously, the tunnelling current is calibrated on a conductive sample at a distance of a few nanometers for which a tunnelling current is detected.

This makes available a reference pair corresponding to a non-zero distance $Z_{tunnel}$ and a tunnelling current $I_0$. By regulating on the value of $I_0$, it is possible to acquire the resonance spectrum of the probe at this distance. The value of the reference amplitude corresponding to this calibrated distance $Z_{tunnel}$ may then be used on another sample (that is of the same kind as the selected reference sample), but that is not conductive, so as to be able to servocontrol the tip in shear-force mode to a distance $Z_{tunnel}$ that is known relative to the reference assistance $Z_0$.

Application to Tip Enhanced Raman Spectrometry

Figure 7A:
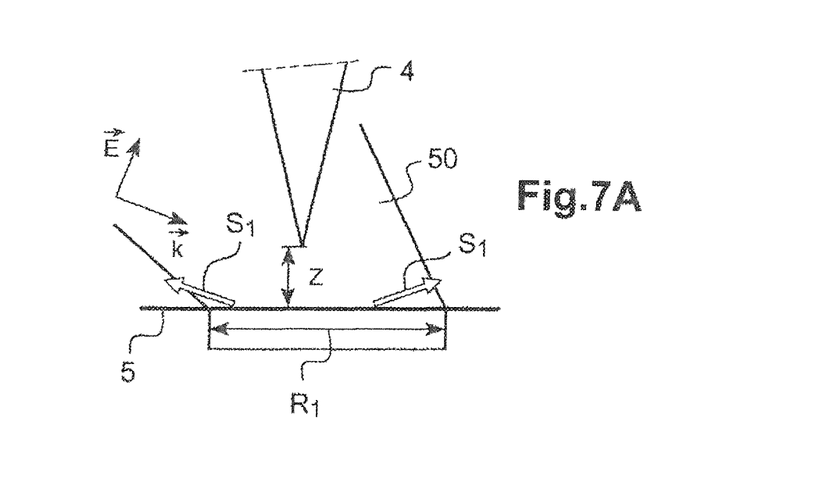
FIGS. 7A and 7B are diagrams showing the spatial resolution of a Raman spectrometer measurement when a local probe tip is situated respectively in the far field (7A) and in the near field (7B) for a nano-Raman or TERS measurement.
Figure 7B:
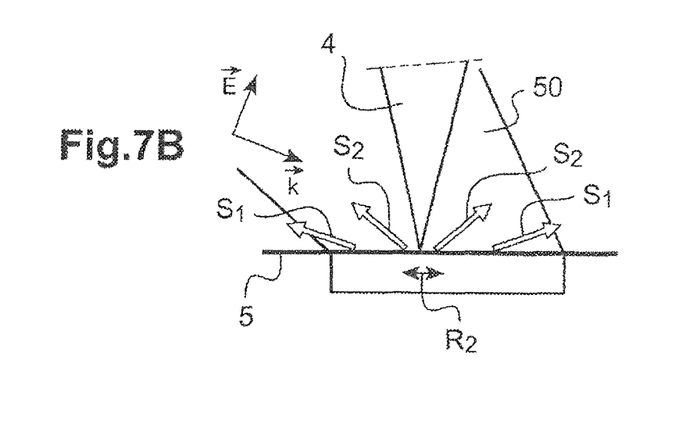

FIGS. 7A-7B show the end of a multimode local probe microscope tip 4 as described with reference to FIGS. 2 and 5A, in a TERS application. An excitation laser beam 50 is focused on the surface of the sample 5. In FIG. 7A, the end of the tip is at a distance Z from the surface of the sample that is greater than a few tens of nanometers, and detection of the Raman signal is then said to be in "far" field. The laser beam incident on the surface of the sample generates a Raman diffusion signal $S_1$. When the tip 4 is at a distance Z corresponding to the far field (FIG. 7A), the spatial resolution $R_1$ of a measurement of the Raman spectrometry signal $S_1$ is detected by the spatial extent of the laser beam 50 on the surface of the sample. This spatial resolution $R_1$ is conventionally of the order of the wavelength of the laser beam. In FIG. 7B, the tip 4 is moved closer to a nonzero distance $Z_0$, corresponding to the "near" field. In this configuration, the excitation laser beam 50 generates in addition to the signal $S_1$, and amplified a Raman diffusion signal $S_2$ in the vicinity of the end of the tip and of the local surface of the sample. The Raman spectrometry signals $S_1$ and $S_2$ are superposed and they are detected simultaneously. Nevertheless, it is observed that the magnitude of the near field Raman signal $S_2$ is much greater than the magnitude of the far field Raman signal $S_1$. The Raman signal detected when the tip 4 has been brought to a distance $Z_0$ is thus essentially representative of the surface of the sample locally around the end of the tip, over an area of dimension $R_2$. This phenomenon corresponds to the tip enhanced Raman spectroscopy (TERS) effect that makes it possible to obtain a Raman signal of spatial resolution that is of sub-nanometer order.

Advantageously, TERS applications, the tip of the microscope is a tip made of a noble metal, gold or silver.

The device and the method of the invention make it possible, by adjusting the distance between the tip and the sample to a distance that is extremely small, to combine a shear-force microscope with a Raman spectrometer in order to perform tip enhanced Raman spectroscopy measurements at a distance that is small and controlled, which was not possible with prior art devices without damaging the tip or the sample. Furthermore, the enhancing effect of the Raman signal is exponential as a function of the reciprocal of the distance Z: the shorter the distance Z, the greater the increase in the Raman signal $S_2$. The Raman signal is observed to increase by three orders of magnitude when the distance between the end of the tip lies in the range 1 nm to 30 nm. This enhancement of the Raman signal in near field therefore requires control of the distance between the vibrating local probe and the surface of the sample to be extremely accurate. This control requires not only that the tip is brought up to a very small distance, but also that this distance is regulated during the transverse vibratory motion of the vibrating probe, while avoiding any contact between the tip and the sample, since that would be destructive.

Figure 8:
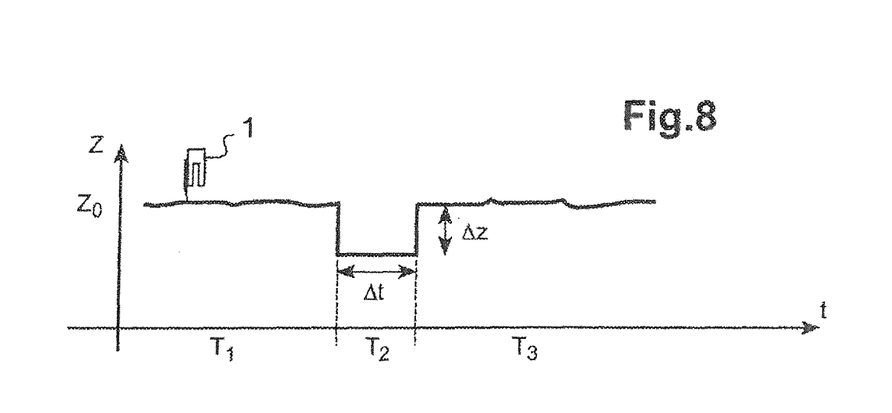
FIG. 8 shows a timing diagram for controlling the tip-to-sample distance, in particular for measurements of the TERS type.

FIG. 8 is a diagram showing timing for recording a nano Raman signal. During the first period T1, the distance between the tip and the sample is servocontroled to a distance $Z_0$ that is calibrated by using the calibration described in the invention, e.g. to 30 nm. During a second period T2 or $\Delta t$, an offset $-\Delta Z$ is applied to bring the tip closer to the surface of the sample to a distance that is small but not zero (by way of example, $-\Delta Z$ is equal to −25 nm, −20 nm, −10 nm, −5 nm). During the period T2, the distance Z is not regulated, but this distance is determined relative to the calibrated distance $Z_0$ and to the known offset $-\Delta Z$: $Z=Z_0\Delta Z$. In synchronous manner, during the second period, opening of the shutter of the Raman spectrometer is triggered (or its detector system is triggered), while the excitation laser beam 50 is focused on the end of the tip 4. A tip enhanced Raman signal $S_2$ is acquired during this period T2. During a third period to T3, the tip is retracted by applying a reverse movement $+\Delta Z$, so as to return to the distance $Z_0$ at which the regulation is performed, and simultaneously the detection shutter is closed. Once calibration has been performed, e.g. for a nano Raman application, $\Delta Z$ and $\Delta t$ are programmable. The mode of operation described with reference to FIG. 8 corresponds to alternating friction force/TERS (shear-force/tapping) operation.

Figure 9:
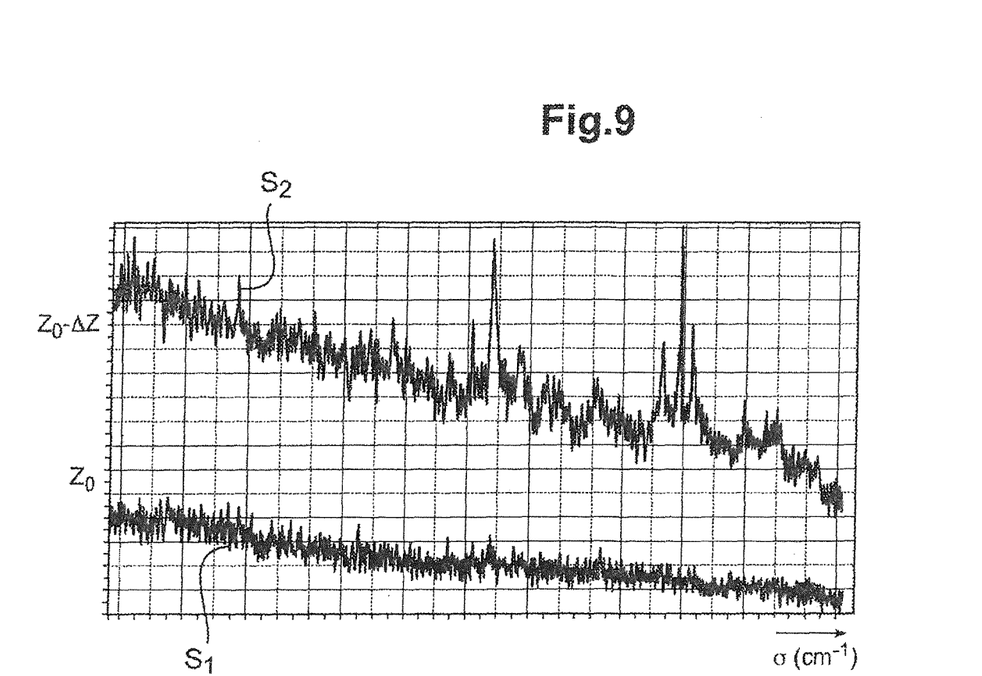
FIG. 9 shows an example of nano-Raman or TERS measurements for two different distances between the end of the tip and the surface of a sample.

FIG. 9 shows the intensities of two Raman spectra for a single sample as a function of wave number $\omega$ ($cm^{-1}$) for two respective distances Z. A first spectrum $S_1$ is obtained for a regulation distance equal to $Z_0$ at 30 nm, and a second spectrum $S_2$ is obtained for a distance equal to $Z_0-\Delta Z$ (15 nm). In the second spectrum $S_2$, there can be seen Raman emission lines characteristic of probed molecules that do not appear on the first spectrum $S_1$. This result illustrates the effect of near field enhancement of the Raman signal, when the tip is brought up to a very small, but nonzero, distance from the surface of the sample.

Invention proposes a multimode local probe microscope that enables measurements to be made simultaneously in friction force (shear-force) mode and in tunnelling mode (STM), with the operation of each mode not affecting the other, and it enables measurements to be made at atmospheric temperature and pressure. The microscope has only two electrical contact points on the probe, and preferably only one common preamplifier in a single electronic circuit having filters that may be active or passive. This multimode local probe microscope makes it possible to regulate very accurately and to calibrate the working distance between the tip and the surface of the sample, in particular for a very small distance, of the order of a few nanometers. This operation makes it possible to combine such a resonant local probe microscope very effectively with a Raman spectrometer in order to acquire enhanced Raman spectrometry measurements. The amplification factor of the TERS Raman signal increases inversely with reduction in the distance zero, thus making it possible to obtain TERS Raman measurements presenting unprecedented sensitivity and spatial resolution simultaneously.

The invention claimed is:

1. A multimode local probe microscope comprising:
   a resonator having an input first electrode and an output second electrode arranged on the resonator;
   excitation mechanism adapted to generate mechanical resonance in the resonator;
   a metal or metal-plated tip having an end of nanometer dimensions, the tip being fastened to the resonator; and
   movement mechanism for imparting relative movement between the resonator and a sample, the movement being adapted to bring the end of the tip up to a distance Z lying in the range 0 to 100 nm from the surface of the sample;
   wherein:
   said tip is electrically connected to said output second electrode, said output second electrode forming a common electrical contact point for collecting firstly a first electrical signal representative of friction forces between the end of the tip and the surface of the sample, and secondly a second electrical signal relating to a tunnelling current between the end of the tip and the surface of the sample; and
   in that the microscope includes:
   amplifier electrically connected to said output second electrode, said amplifier being adapted to amplify the second signal relating to the tunnelling current;
   processor adapted to process separately firstly the first signal relating to friction forces and secondly the second signal relating to the tunnelling current; and
   regulator adapted to regulate the distance Z between the end of the tip and the surface of the sample, regulation in a first mode being as a function of the first signal representative of friction forces, and regulation in a second mode being as a function of the second signal relating to the tunnelling current.

2. A multimode local probe microscope according to claim 1, wherein said processor means comprise active or passive filter, said filter being adapted to separate firstly the first signal relating to friction forces and secondly the second signal relating to the tunnelling current as a function of their respective frequencies.

3. A multimode local probe microscope according to claim 2, wherein said filter comprise a bandpass filter adapted to filter said first signal relating to friction forces spectrally, and a lowpass filter adapted to filter said second signal relating to the tunnelling current spectrally.

4. A multimode local probe microscope according to claim 1, wherein the tip is made of or covered in a metal preferably selected from gold and silver.

5. A multimode local probe microscope according to claim 1, said microscope including a scanning mechanism for scanning the tip relative to the surface of the sample.

6. A multimode local probe microscope according to claim 1, wherein the quartz resonator in the form of a tuning fork having a first branch and a second branch, the input first electrode being arranged on the first branch, and the output second electrode being arranged on the second branch.

7. A tip enhanced Raman microscope having a multimode local probe microscope according to claim 1, said Raman microscope comprising a Raman spectrometer, mechanism for focusing an excitation laser beam on the end of the tip of the microscope, and detector for detecting a Raman diffusion signal generated by the sample in the vicinity of said tip.

8. A tip enhanced Raman microscope according to claim 7, said microscope comprising a mechanism for triggering detection of the Raman diffusion signal and synchronisation mechanism that are connected firstly to the mechanism for triggering detection and secondly to the mechanism for regulating the distance Z between the tip and the sample in such a manner as to synchronise said mechanism for triggering detection of the Raman diffusion signal and said regulator while bringing the tip to a predetermined distance $Z_0-\Delta Z$.

9. A method of regulating the distance Z between the surface of the sample and the end of the tip of a multimode local probe microscope according to claim 1, wherein calibration method comprises the following steps:
   generating mechanical resonance in the resonator suitable for producing vibration at the end of the local probe tip;
   bringing the tip towards the surface of a reference sample;
   simultaneously detecting a first electrical signal relating to friction forces between the end of the tip and the surface of the reference sample, and a second signal relating to a tunnelling current generated between the end of the tip and the surface of the reference sample;
   for said reference sample, determining a reference distance at which a reference tunnelling current appears, said reference distance corresponding to a distance for which said second signal is greater than or equal to a predetermined tunnelling current threshold for said reference sample;
   measuring a reference value of the first signal relating to friction forces on said reference sample at said reference distance at which tunnelling current appears; and
   regulating the first signal relating to friction forces for any type of sample of the same nature as the reference sample as a function of said reference value for the first signal relating to friction forces on said reference sample at said reference distance at which tunnelling current appears.

10. Regulation method according to claim 9, wherein the reference distance is greater than zero and less than or equal to 10 nm.

* * * * *